United States Patent
Korth et al.

(10) Patent No.: US 7,932,043 B2
(45) Date of Patent: Apr. 26, 2011

(54) USE OF MONOCLONAL ANTIBODIES TO DISTINGUISH PROTEIN CONFORMATIONAL ISOFORMS

(75) Inventors: Carsten Korth, Duesseldorf (DE); Vishwanath R. Lingappa, San Francisco, CA (US)

(73) Assignee: The University of California at San Francisco, San Francisco, CA (US)

( * ) Notice: Subject to any disclaimer, the term of this patent is extended or adjusted under 35 U.S.C. 154(b) by 503 days.

(21) Appl. No.: 10/490,977

(22) PCT Filed: Aug. 18, 2003

(86) PCT No.: PCT/US03/25994
§ 371 (c)(1),
(2), (4) Date: Apr. 1, 2005

(87) PCT Pub. No.: WO2004/033628
PCT Pub. Date: Apr. 22, 2004

(65) Prior Publication Data
US 2007/0281318 A1    Dec. 6, 2007

Related U.S. Application Data

(60) Provisional application No. 60/417,886, filed on Oct. 10, 2002.

(51) Int. Cl.
*G01N 33/53* (2006.01)
*C07K 16/00* (2006.01)

(52) U.S. Cl. ........................................ 435/7.1; 530/387.1
(58) Field of Classification Search .................. None
See application file for complete search history.

(56) References Cited

U.S. PATENT DOCUMENTS
2002/0137915 A1    9/2002    Lingappa et al.

FOREIGN PATENT DOCUMENTS
WO    WO 97/10505 A    3/1997

OTHER PUBLICATIONS

Wong et al. (2000) Biochemical and Biophysical Research Communications. 276: 1217-1224.*
Kramer et al. (2001) Journal of Biological Chemistry. 276(20): 16711-16719.*
Krasemann, S., et al. "Induction of Antibodies against Human Prion Proteins (PrP) by DNA-mediated Immunization of $PrP^{0/0}$ Mice" *J. Immunolog. Methods* 199 (2): 109-118 (1996).
Yokoyama, T., et al. "In Vivo Conversion of Cellular Prion Protein to Pathogenic Isoforms, as Monitored by Conformation-specific Antibodies" *J. Biol. Chem.* 276 (14): 11265-11272 (2001).
Hay, B., et al. "Biogenesis and Transmembrane Orientation of the Cellular Isoform of the Scrapie Prion Protein" *Mol. Cell. Biol.* 7 (2): 914-920 (1987).
Barry, R. A., et al. "Monoclonal Antibodies to the Cellular and Scrapie Prion Proteins" *J. Infectious Diseases* 154 (3): 518-521 (1986).
Holscher, C., et al. "Prion Protein Contains a Second Endoplasmic Targeting Signal Sequence Located at its C Terminus" *J. Biol. Chem.* 276 (16): 13388-13394 (2001).
Korth et al, (1997) *Nature* vol. 390(No. 6655):p. 74-77.
Hegde et al, (1999) *Nature* vol. 420(No. 6763):p. 822-826.
Laffling et al, (2001) *Neuroscience Letters* vol. 300(No. 2):p. 99-102.
Hardt et al, (2000) *Journal of Comparative Pathology* vol. 122(No. 1):p. 43-53.
Bodemer, W., (1999) *Naturwissenschaften* vol. 86(No. 5):p. 212-220.
Harmeyer et al, (1998) *Journal of General Virology* vol. 79(No. 4):p. 937-945.
Krasemann et al, (1996) *Molecular Medecine* vol. 2(No. 6):p. 725-734.
Peretz et al, (2001) *Nature* vol. 412(No. 6848):p. 739-743.
Graner et al, (2000) *FEBS Letters* vol. 482(No. 3):p. 257-260.
Shyng et al, (1995) *Journal of Biological Chem.* vol. 270(No. 50):p. 30221-30229.
Rutkowski et al, (2001) *Proc. of the Nat.Acad. of Sci.* vol. 98(No. 14):p. 7823-7828.
Hegde et al, (1998) *Science* vol. 279(No. 5352):p. 827-834.
Hornemann et al, (1997) *FEBS Letter* vol. 413(No. 2):p. 277-281.

* cited by examiner

*Primary Examiner* — Zachariah Lucas
*Assistant Examiner* — Michelle Horning
(74) *Attorney, Agent, or Firm* — Quine Intellectual Property Law Group; Stacy Landry

(57) ABSTRACT

Methods of preparing monoclonal antibodies that differentially bind to a single conformer of a protein of interest are described. Passive immunization using these antibodies as well as use of conformer-specific antibodies as diagnostic reagents for the purpose of stratification of patient populations with regards to disease outcome, drug efficacy or drug sensitivity is also disclosed as well as active immunization with the protein conformer. In the screening techniques, detection can be for example by tissue immunostaining, western blotting or solution IP. A specific mab termed 7VC which shows conformation specificity to CtmPrP, a prion protein conformer that triggers neurodegeneration under specific assay conditions of pH and copper concentration, is described. A second specific antibody termed 19B10 shows conformation specificity for NtmPrP, a prion protein conformer that downregulates total PrP expression and effects cell differentiation.

5 Claims, 12 Drawing Sheets

| Peptide from haPrP | IR | Sequence |
|---|---|---|
| haPrP 23-98 | ++ | |
| haPrP 90-114 | - | |
| haPrP 171-231 | - | |
| ha PrP 214-231 | - | |
| haPrP 51-65 | - | PQGGGTWGQP GGGW |
| haPrP 65-79 | + | WGQP GGGWGQP GG |
| haPrP 72-86 | ++ | GWGQP GGGWGQP |
| haPrP 86-100 | ++ | GGGWGQGGGT NQWN |

Fig. 5

USE OF MONOCLONAL ANTIBODIES TO DISTINGUISH PROTEIN CONFORMATIONAL ISOFORMS

This application is a 371 of PCT/US2003/25994, filed Aug. 18, 2003, which claims benefit of U.S. Provisional Application Ser. No. 60/417,886, filed Oct. 10, 2002.

STATEMENT OF GOVERNMENT RIGHTS

This invention was made with government support under Grant No. NS37365 awarded by the National Institutes of Health. The government has certain rights in the invention.

FIELD OF THE INVENTION

The present invention relates to methods and compositions for distinguishing protein conformation isoforms and for diagnosis and treatment of diseases related to a particular conformational isoform. The invention is exemplified by preparation of monoclonal antibodies that differentially bind to prior protein isoforms associated and their use in detection and/or inhibition of of prion disease.

BACKGROUND

Protein biogenesis in the secretory pathway involves several processes that overlap in time with polypeptide chain synthesis. First, the nascent polypeptide chain must be targeted correctly to the membrane of the endoplasmic reticulum (ER). Then, its translocation to the lumen of the ER is initiated. Folding of the polypeptide chain has to begin early in its translocation. During and immediately after translocation, posttranslational modifications occur, and decisions are made by the cell regarding degradation of undesired chains, including translocation back to the cytoplasm and degradation by the proteasome. Of the processes contemporaneous with translocation, perhaps the most profound is protein folding, because it is a crucial step in the decoding of the information in the genome. A misfolded protein may be as bad as, or worse, than not having the protein at all. If proteins have multiple folded states with distinct functions, the precise pathway of folding and its regulation will determine which function is actually expressed, and to what extent.

A fundamental dogma of modern biology is that primary structure determines secondary structure, which together with appropriate post-translational modifications such as disulfide bond formation, determines the tertiary (and quaternary) protein structures. This organization, from primary structure secondary structure tertiary structure, constitutes a "first order" organizing principle for protein folding. Implicit in the term "structure" is the notion or a unique, stable entity; but protein structure is a statistical concept. Native protein conformations are energetically preferred relative to unfolded, denatured forms of the same chains; but the energetic preference is modest (10 kCal/mole), which means that proteins are dynamic, fluctuating entities, and even "stable" proteins will unfold, to some degree, transiently.

Translocation overlaps with protein folding, therefore one would expect that, in the course of evolution, these two processes would have influenced one another. Folding pathways may have been modified to accommodate the needs of translocation; translocation pathways may have been modified to accommodate the needs of folding. A growing body of literature provides support for both of these possibilities. The most dramatic example to date of translocational regulation, with implications for folding, is seen in the biogenesis of the prion protein (PrP). In the case of PrP, a homogeneous population of nascent chains results in three topological forms. One of them, secPrP, appears to be fully translocated (secreted) across the ER membrane and tethered by a C-terminal glycolipid anchor; this is the form observed in normal brain. Although the function of secPrP is unknown, it seems likely, by analogy to other glycolipid anchored proteins, to have signaling functions in the nervous system. A recently demonstrated anti-apoptotic function appears consistent with this role. The other two forms of PrP span the membrane once in opposite orientations, with a membrane-spanning stretch at approximately amino acids 112±30. By contrast, the other two forms of PrP are made as singly-spanning membrane proteins in opposite orientations with either the N- or C-terminus in the ER lumen (termed $^{Ntm}$PrP and $^{Ctm}$PrP, respectively). $^{Ctm}$PrP triggers spontaneous neurodegeneration when overexpressed. Furthermore, in infectious prion disease, CtmPrP appears to be induced just prior to onset of clinical signs, suggesting that it initiates a final common pathway to neurodegeneration. Other studies implicate an as yet unknown glycoprotein of the ER membrane as a translocation accessory factor (TrAF) that "protects" the normal brain from expression of CtmPrP by directing nascent PrP chains to the pathway leading to SecPrP.

The distinction between SecPrP and CtmPrP is usually made on topological grounds. However, these two polypeptides of identical sequence also differ in their conformation. This was demonstrated by their differential sensitivity to limited protease digestion in non-denaturing detergent solutions. Thus, translocational regulation appears to be a means of generating multiple forms of PrP that differ in both conformation and function. The machinery (i.e. a TrAF) that directs nascent PrP chains to make SecPrP rather than CtmPrP, may itself be regulated, based on the ability of scrapie infection to increase the amount of CtmPrP detectable in brain. Although PrP is currently the best example of translocational regulation, there is evidence for similar principles being utilized by a broader set of proteins. Together, these observations lead to a new principle: a protein's conformation is determined not just by its primary amino acid sequence, but also by proteins such as TrAF, that influence which of two or more different functional conformational outcomes actually occur or predominate.

It therefore is of interest to determine if complex secretory or integral membrane proteins can have multiple distinct functional folded states. At present, the major limitation to testing these and other hypotheses of conformational control is a lack of tools to recognize the heterogeneity of functional protein conformations. But for the fortuitous coincidence that, in PrP, conformational heterogeneity was expressed as topological heterogeneity, it might not yet have been detected. Better tools such as panels of conformation-specific monoclonal antibodies that would allow relative reactivities of subpopulations of newly synthesized proteins to be scored, and thereby define conformational differences are needed. This approach would allow a catalogue of the conformational states utilized by a given protein in health and during the progression to disease as well as a means for inhibiting the disease.

SUMMARY OF THE INVENTION

Novel compositions based on conformational specific monoclonal antibodies and their use for diagnosis and treatment of diseases related to particular protein conformers are provided. For monoclonal antibody production, animals are immunized with antigens, optionally with adjuvant, comprising at least one conformer of a protein of interest. B cells from an immunized host are used to prepare hybridomas which produce monoclonal antibodies to one or more conformers of the protein of interest that share a common epitope. The monoclonal antibodies are then screened to identify those that exhibit differential binding to individual conformers of the protein of interest. The monoclonal antibodies find use in detection assays for conformer mediated diseases and for treatment of the disease via active or passive immunization. An unconventional approach to screening is provided, involving solution immunoprecipitation of defined conformers with individual hybridomas in order to identify monoclonal antibodies that bind selectively but perhaps weakly to a specific conformer. These monoclonal antibodies then are characterized and used to screen patient samples including serum to identify conformer-specific features and associations of disease and disease pathogenesis and/or to promote differentiation of cells expressing PrP and or to inhibit PrP expression.

BRIEF DESCRIPTION OF THE DRAWINGS

FIG. 5: Enzyme-linked Immunoadsorbent assay (ELISA) for peptide binding was perfomed as follows: Streptavidin-coated ELISA plates (96-well format; Roche, USA) were coated with 1 µg /well N-terminally biotinylated peptide of the sequence indicated for 2 hours at 37° C. ELISA plates were then washed with phosphate-buffered saline and blocked with 5% bovine serum albumin for one hour at 37° C. After washing, undiluted and a dilution series of mAB 7VC supernatants or control antibodies in TBS-T were incubated with the coated wells for 2 hours at 37° C. After washing, secondary goat anti-mouse IgG, alkaline phosphatase labeled (Pierce, USA), was incubated at a 1:1000 concentration in TBS-T for 45 minutes at room temperature. After washing, substrate (p -nitrophenyl phosphate; Sigma, USA) was added to the wells and a yellow discoloration monitored in an ELISA reader.

DESCRIPTION OF THE SPECIFIC EMBODIMENTS

Figure 1:
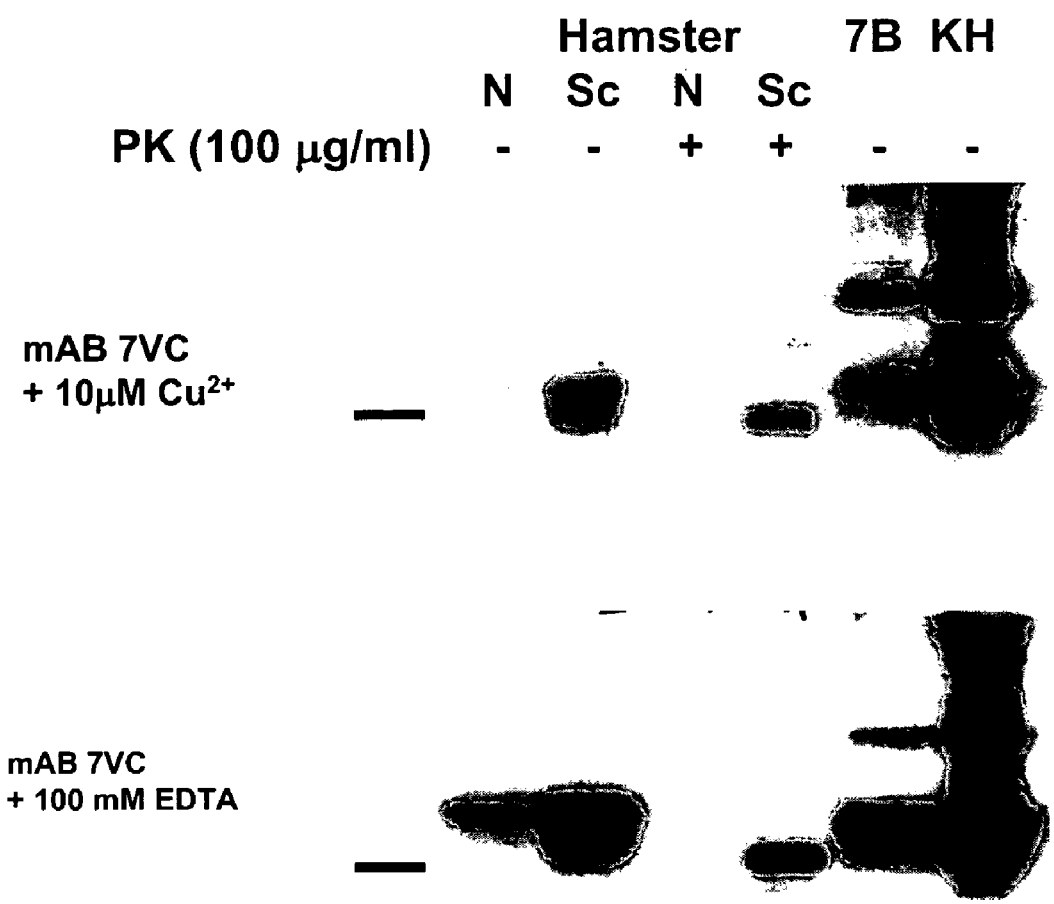
FIG. 1: Protease digestion with Proteinase K (Merck, Germany) 100 µg/ml was performed for 1 hour at 37° C. and stopped with 5 mM phenylmethanesulfonyl fluoride (PMSF; Sigma, USA).
Figure 2:
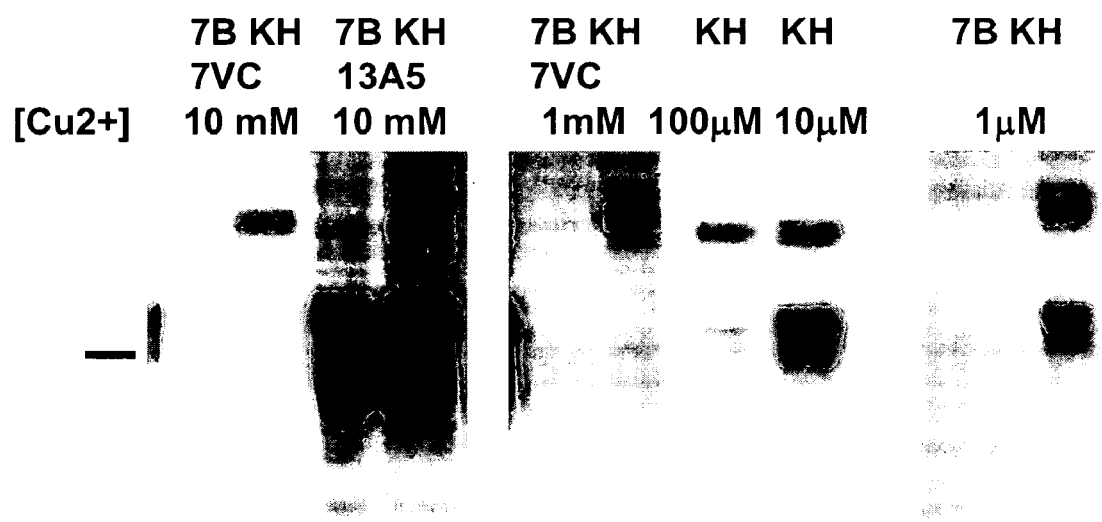
FIG. 2: mAB 13A5 was used in a 1:5000 dilution from ascites.
Figure 3:
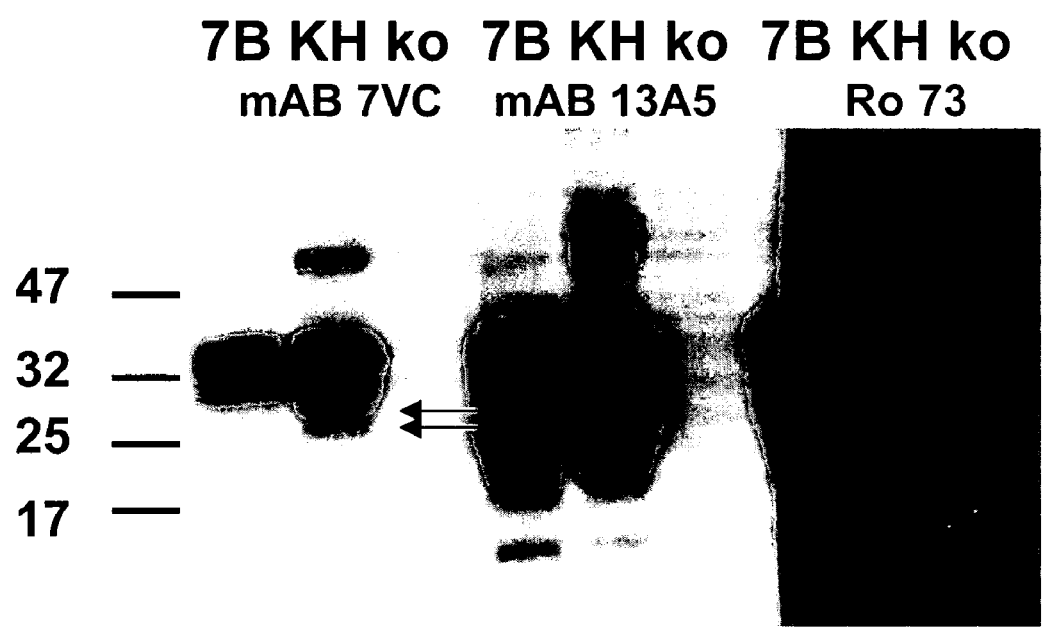
FIG. 3: mAB 13A5 and Ro73 antiserum were used at 1:5000 dilution.
Figure 4:
FIG. 4: PNGase F and Endo H were purchased from New England Biolabs (NEB, USA) and used according to the manufacturer's protocol.
Figure 6:
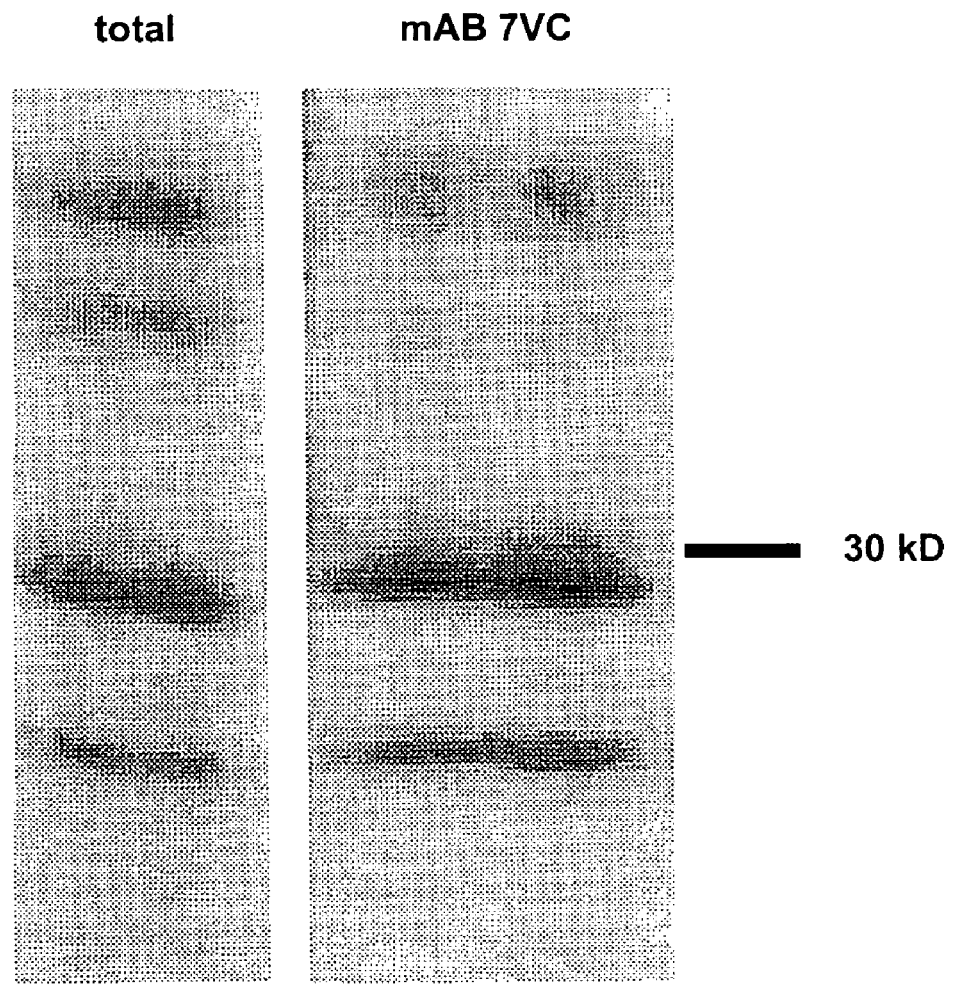
FIG. 6: In vitro translated, radioactive $S^{35}$-labeled PrP was produced as described by Hay et al., 1987, Hegde et al., 1998 Science 279, 827-834, and Hegde et al., 1999). Total products were then incubated with mAB 7VC supernatant or control antibodies and 15 µl protein A (Gibco/Invitrogen, USA) and incubated on a rotating wheel for 3 hours at 4° C. Products were then washed three times with homogenisation buffer, boiled in sample buffer, and loaded on a 15% SDS gel. Gels were dried and exposed to hyperfilm (Amersham Pharmacia, USA).
Figure 7:
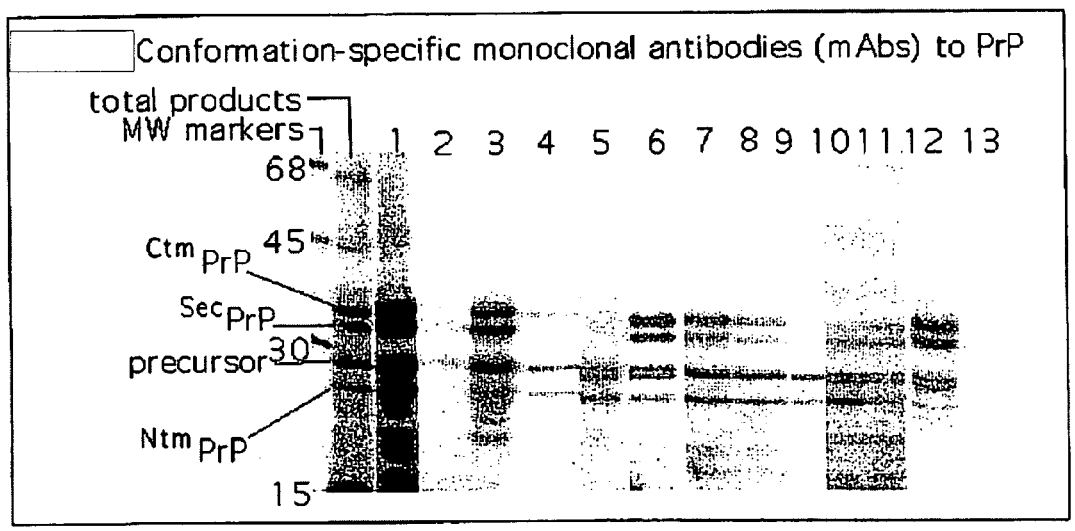
FIG. 7 shows radiolabelled cell-free translation products representing roughly equivalent amounts of each PrP topological form and precursor were used to screen 1500 individual hybridoma supernates. Lanes 1-13 were immunoprecipitated by selected clones. Lane 1 shows a "strong reactor" under conditions which lack conformational specificity. Lane 13 shows the results with no added antibody. Antibodies used in Lanes 2-12 show varying degrees of conformation specificity, ranging from highly Ntm -specific (lane 10) to preferentially secretory (lane 3) and Ctm (lane 10). In most cases reactivity to precursor was observed, but since precursor is an artifact of cell-free translation which is not observed in vivo (due to the efficiency of targeting), its presence can be ignored. Immunogen for this fusion was denatured recombinant PrP. It is likely that using native Ctm vs Sec PrP as immunogen would give more directed conformation specific responses, as proposed.

In accordance with the subject invention compositions are provided that are individual conformers of a protein of interest and monoclonal antibodies thereto. Preferably the conformers are produced using a system, such as a cell-free translation system, that permits selective synthesis of a single conformer of the protein of interest so that monoclonal antibodies can be identified that differentially bind to a single conformer so that conformers that may share at least one epitope can be distinguished. The term "conformer" refers to two or more proteins having at least substantially the same amino acid sequence, but having heterogeneity in structure (physical topology or topography) and function. By topology is intended the different placement of particular parts of the protein in particular subcellular compartments, e.g. C-cytosolic as compared to N-cytosolic, and. topography intends change in external conformation or shape in space, (i.e. different three -dimensional shape due to differences in folding/conformation), which includes stable and/or transient association with other proteins. As used herein, polypeptides of substantially the same amino acid sequence are those with conservative amino acid substitutions (i.e. a small or large side chain for a small or large side chain, respectively; or an acidic, basic, polar or hydrophobic side chain for an acidic, basic, polar or hydrophobic side chain, respectively), that do not alter protein conformation or topology. The protein conformation changes are due to differences in folding or to post-translational modifications and are not a result of differences in the amino acid sequence.

Animals, including humans for diagnosis and/or treatment and/or inhibition of the effects of a particular disease-associated conformation of the protein of interest, are immunized for the production of antisera containing antibodies that specifically bind to a disease-associated conformation of the protein of interest. B cells from the immunized animal host can be used to produce hybridomas that produce monoclonal antibodies having the same specificity spectrum. Recombinant immunoglobulin light chain and/or heavy chains and functional fragments thereof can be made recombinantly by isolating nucleic acid encoding the monoclonal antibody light and heavy chains or functional portions thereof and expressing it in a prokaryotic host cell such as E. coli or a eukaryotic host cell such as a yeast or mammalian cell. The recombinant antibodies can include alterations in the amino acid sequence to provide for desired characteristics, for example changes can be made in the variable region to provide improved antigen binding characteristics. Preferably, the antibodies produced and/or administered for use in treating the effects of a particular disease-associated conformation of the protein of interest, are neutralizing antibodies. As used herein, the term antibody refers to entire antibody molecules comprising both heavy and light chains, but also to any fragment of said antibody such as $(Fab)_2$, Fab, Fv fragments and ScFv fragments that retain the desired specificity of binding to individual protein conformers. As used herein, the term "neutralizing", when referring to antibodies, means that such antibodies bind to individual protein conformers found in bodily fluids of subjects with a disease related to a specific protein conformer. In some instances, the antibody may act to prevent binding of the protein to cellular receptors; preferably such an antibodies has a sufficient affinity for the protein conformer that they can remove receptor bound conformer from its receptor when the conformer is bound to its receptor.

Monoclonal antibodies can be produced to corroborate the functional assay results and show, based on epitope mapping, that (i) antibodies to the same epitopes do not bind proteins that contain essentially the same amino acid sequences; and (ii) alternative folding of proteins masks or uncovers epitopes and renders them immunologically, and thus structurally, distinct. Sequencing of the cloned suspected conformer is conducted to demonstrate that the proteins have essentially the same amino acid sequence. Thus, monoclonal antibodies to a mapped epitope can be used to identify conformers with different structural, and, by implication, functional characteristics which can be used as specific drug targets, thus decreasing potential side effects. Monoclonal antibodies can be used with unpurified lysates from either transfected cells or a programmed cell-free system.

The subject invention offers several advantages over existing technology. The problem of detecting heterogeneity in biological samples is compounded by several issues: first, heterogeneity can only be detected with reagents (for example monoclonal antibodies) that distinguish one conformer from another. But most conformers share many epitopes and so, only a small subset of monoclonal antibodies raised to a given conformer are absolutely or relatively conformer specific, and many monoclonal antibodies are indistinguishable in reactivity to different conformers. The subject invention allows one to distinguish the "needle in the haystack" that is, the rare monoclonal antibody that is absolutely or relatively conformer specific, perhaps of low affinity because of its conformer specificity, i.e. restriction of its epitope to a small part of a conformer's surface, from other monoclonals that are not conformer specific. Second, the time to determine if a new hybridoma is conformer specific is limited to as little as days before the hybridoma dies or is overgrown by competing clones. The subject invention provides strategies to overcome these barriers to identification of relevant monoclonal antibodies These valuable but rare monoclonals when used for example in screening assays offer the advantage that they are able to distinguish individual conformers in a conformer mix in patient samples such as blood samples. Additionally they offer the advantage that they provide a means of distinguishing conformers rapidly and with extremely high sensitivity and specificity with minimal perturbation of conditions such as would occur with protease digestion and other more conventional probes of conformation and topology.

Antigens that are used for immunization can include a mixture of conformers but preferably are individual conformers of a protein of interest. Methods that can be used for making individual conformers-antigens include an in vitro translation system (see for example Hay et al., 1987 Mol. Cell Biol. 7:914-919; Hegde et al. (1998) Science 279, 827-834; and Hegde et al. (1999) Nature 402, 822-826. Attempts are made to skew the conformational mix synthesized, allowing minor and transient conformers to be magnified and stabilized and therefore more readily detected and characterized, so that they can be distinguished from the normally dominant conformers. This can be done in various ways, including by swapping signal sequences that are cleaved or by expressing the proteins in fractionated and reconstituted systems that modify the native conformer mix through actions (or their absence) in trans, by TrAF depletion or by other means.

For the immunization any methods known to those of skill in the art can be used. If only small amounts of antigen are available, protocols such as those described by (Blachere et al., (1997) J Exp Med 186, 1315-1322 and (Castellino et al., (2000) J Exp Med 191, 1957-1964 can be used. Small (microgram amounts) of a protein such as heat shock protein (HSP) and a conformer of a protein of interest are combined and then used for immunization of a host animal. The route of administration can be intracutaneous subcutaneous, intramuscular, intraperitoneal or intravenous route and the method of administration is according to standard protocols known to those of skill in the art. Optionally, an adjuvant such as Freund's complete adjuvant, RIBI or aluminium hydroxide or a recombinant cytokines such as interleukin-2 can be used with the antigen.

Monoclonal antibodies can be prepared in any number of ways known to those skilled in the art (see, for example, Kohler et al., Nature, 256: 495-497 (1975) and Eur. J. Immunol. 6:511-519 (1976); Milstein et al., Nature 266: 550-552 (1977), Koprowski et al., U.S. Pat. No. 4,172,124; Harlow, E. and D. Lane, 1988, Antibodies: A Laboratory Manual, (Cold Spring Harbor Laboratory Press, Cold Spring Harbor, N.Y. (1989); Current Protocols In Molecular Biology, Vol. 2 (Supplement 27, Summer 1994), Ausubel, F. M. et al., Eds., (John Wiley & Sons: New York, N.Y.), Chapter 11, (1991)). In this process, splenocytes or lymphocytes from an animal that has been injected with antigen are fused with a tumor cell line, thus producing hybrid cells or "hybridomas" which are both immortal and capable of producing the genetically coded antibody of the B cell. The hybrids thus formed are segregated into single genetic strains by selection, dilution, and regrowth, and each strain thus represents a single genetic line. They therefore produce immunoreactive homogeneous antibodies against a desired antigen. Hybridoma technology generally uses fusion of murine lines, but human-human hybridomas (Olsson, L. et al., Proc. Natl. Acad. Sci. (USA), 77: 5429 (1980)); human-murine hybridomas (Schlom, J., et al. (ibid) 77: 6841 (1980)) and several other xenogenic hybrid combinations also been reported. Cells which produce antibodies with the desired binding properties are selected by a suitable assay, such as a serological assay, including enzyme-linked immunosorbent assay (ELISA).

Functional binding fragments of monoclonal antibodies also can be produced by, for example, enzymatic cleavage or by recombinant techniques. Enzymatic cleavage methods include papain or pepsin cleavage to generate Fab or $F(ab')_2$ fragments, respectively. Antibodies also can be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH, domain and hinge region of the heavy chain. Functional fragments of the monoclonal antibodies retain at least one binding function and/or modulation function of the full-length antibody from which they are derived. Preferred functional fragments retain an antigen-binding function of a corresponding full-length antibody (e.g., retain the ability to bind an epitope of a conformer). In another embodiment, functional fragments retain the ability to inhibit one or more functions characteristic of a protein or peptide conformer, such as a binding activity, a signaling activity, and/or stimulation of a cellular response. For example, in one embodiment, a functional fragment can inhibit the HIV capsid assembly.

One method of developing conformer specific antibodies is to immunize knock-out mice that lack a functional gene for the protein of interest with a putative conformer of the protein of interest Knockout mice can be produced using standard techniques known to those skilled in the art (Capecchi, Science (1989) 244:1288; Koller et al. Annu Rev Immunol (1992) 10:705-30; Deng et al. Arch Neurol (2000) 57:1695-1702); the gene corresponding to the protein against which monoclonal antibodies are to be raised is knocked out, e.g. HP68. A targeting vector is constructed which, in addition to containing a fragment of the gene to be knocked out, generally contains an antibiotic resistance gene, preferably neomycin, to select for homologous recombination and a viral thymidine kinase (TK) gene. Alternatively, the gene encoding diphtheria toxin (DTA) can be used to select against random insertion. The vector is designed so that if homologous recombination occurs the neomycin resistance gene is integrated into the genome, but the TK or DTA gene is always lost Murine embryonic stem (ES) cells are transfected with the linearized targeting vector and through homologous recombination recombine at the locus of the targeted gene to be knocked out. Murine ES cells are grown in the presence of neomycin and gancyclovir (for TK), a drug that is metabolized by TK to produce a lethal product. Thus cells that have undergone homologous recombination are resistant to both neomycin and ganciclovir. Vectors containing DTA kill any cell that codes for the gene, so no additional drug is required in the cell culture medium. Southern blotting hybridization and PCR are used to verify the homologous recombination event, techniques well known to those skilled in the art.

To generate a mouse carrying a disrupted targeted gene, positive ES cells are propagated in culture to differentiate and the resulting blastocyte is implanted into a pseudopregnant female. Alternatively the ES cells are injected back into the blastocoelic cavity of a preimplantation mouse embryo and the blastocyte is then surgically implanted. The transfected ES cells and recipient blastocytes can be from mice with different coat colors, so that chimeric offspring can be easily identified. Through breeding techniques homozygous knock-out mice are generated. Tissue from these mice is tested to verify the homozygous knockout for the targeted gene, for example using PCR and Southern blotting hybridization.

In an alternate method, gene targeting using antisense technology can be used (Bergot et al., JBC (2000) 275:17605-17610). The homozygous knockout mice are immunized with purified host protein peptides, both native and denatured recombinant protein. Following subsequent boosts, at 3 and 6 weeks, with the immunogen, the mice are sacrificed and spleens taken and fusion to myeloma cells carried out (Korth et al. Methods in Enzymol. (1999) 309:106). Antibodies from individual hybridomas are screened for conformational specificity, i.e., binding with substantial specificity to a single conformer. The screening process is carried out with radiolabeled protein products produced in the cell-free translation system or radiolabeled media or cell extracts chosen to enrich one versus another conformer.

These products are immunoprecipitated using hybridoma supernatant and run on a SDS-PAGE gel. Preferably cell-free extracts are used due to the possibility that the use of transfected cells would result in protein-protein interactions that would block antibodies from binding a specific epitope, thus masking a potential conformer. The use of an immunoprecipitation screen with radiolabeled translation products, the conformation of which has been skewed (e.g. by swapping of signal sequences), and screening for weak responders are keys that distinguish this screen from a conventional approach to monoclonal antibody production.

A variation of the method for screening for monoclonal antibodies that exhibit differential binding is to vary the pH, ionic composition of the assay, and/or other conditions such as presence of serum or serum proteins, or metal ions to which the protein of interest binds, such as copper. These conditions that may vary from antibody to antibody. Other means of obtaining differential binding of monoclonal antibodies to specific conformers can be used. As an example, specific conformational epitopes defined by such monoclonal antibodies are used as tags or reporters of conformation change by engineering coding regions of various sizes into other target proteins. Thus the tag can be turned "on" or "off" simply by varying the ionic conditions, and a conformational change can be induced or suppressed by the change in ionic or other conditions. The use of 96 well plates for screening streamlines the process, allowing a single technician to screen up to 1000 individual hybridomas in a single day.

Antibodies also can be prepared by recombinant means. Messenger RNA coding for a heavy or a light chain is isolated from a suitable source, such as mature B cells or a hybridoma culture making antibodies of the desired specificity using standard techniques of RNA isolation, and the use of oligo-dT cellulose chromatography to segregate the poly-A mRNA. The poly-A mRNA may be fractionated to obtain sequences of sufficient size to code for the amino acid sequences in the light or heavy chain of the desired antibody. A cDNA library is then prepared from the mixture of mRNA using a suitable primer, preferably a nucleic acid sequence which is characteristic of the desired cDNA. Such a primer may be hypothesized and synthesized based on the amino acid sequence of the antibody if the sequence is known. In the alternative, cDNA from unfractionated poly-A mRNA from a cell line producing the desired antibody or poly-dT also can be used. Cloning vectors containing the resulting cDNA are prepared and used to transform a suitable host cell strain, typically *E. coli*. Successful transformants are identified by means of, for example, tetracycline resistance or other phenotypic characteristic residing on the cloning vector plasmid. The transformant cultures are then probed with suitable nucleotide sequences containing bases known to be complementary to desired sequences in the cDNA. Plasmids from clones which successfully hybridize are isolated and sequenced by means known in-the art to verify that the-desired portions of the gene are present. The desired gene fragments are excised and tailored to assure appropriate reading frame with the control segments when inserted into suitable expression vectors. The tailored gene sequence is then positioned in a vector which contains a promoter in reading frame with the gene and compatible with the proposed host cell. A number of plasmids which already contain the appropriate promoters, control sequences, ribosome binding sites, and transcription termination sites, as well as convenient markers are known to those of skill in the art.

The genes also may be tailored to produce modified antibodies. For example, a mammalian heavy chain may not be derived entirely from a single source or single species, but portions of a sequence can be recovered from differing pools of mRNA, such as murine-murine hybridomas, human-murine hybridomas, or B cells differentiated in response to a series of antigen challenges. The desired portions of the sequences in each case can be recovered using the probe and analysis techniques described above, and recombined in an expression vector. Such chimeric chains can be constructed of any desired length; hence, for example, a complete heavy chain can be constructed, or only a sequence for the Fab region thereof.

For construction of chimeric antibodies in which for example, the variable sequence is derived separately from the constant sequences, desired portions of the genes encoding parts of the heavy and light chains from suitable, differing, sources are recovered and then ligated to reconstruct the gene coding for each chain. For example, portions of the heavy chain gene and of the light chain gene which encode the variable sequences of antibodies produced by a murine hybridoma culture are cloned and gene fragments encoding the constant regions of the heavy and light chains for human antibodies are cloned from, for example, human myeloma cells. The variable portions of the mouse gene are then ligated to the constant regions of the human gene for each of the two chains. Rather than splicing portions of the chain(s), suitable amino acid alterations, deletions or additions are made using available techniques such as mutagenesis, to provide for desired characteristics.

The gene coding for the light chain and that coding for the heavy chain can be inserted into separate expression plasmids, or together in the same plasmid, so long as each is under suitable promoter and translation control, and used to transform suitable cells which are grown under conditions appropriate to the production of the desired protein. Such conditions are primarily mandated by the type of promoter and control systems used in the expression vector, rather than by the nature of the desired protein. The protein thus produced is then recovered from the cell culture by methods known in the art, the choice of which is necessarily dependent on the form in which the protein is expressed. When heavy and light chains are coexpressed in the same host, the isolation procedure is designed so as to recover reconstituted antibody. This can be accomplished using methods known to those of skill in the art.

Specific antibody fragments of the invention such as (Fab)$_2$, Fab, and Fv fragments, wherein the specificity against a particular protein conformer is conserved, can be obtained by chemical cleavage of complete antibodies according to well-known methods (see for example Weir (1986). Handbook of Experimental Immunology. 4th Edition. Blackwell, Oxford. Vol. 1. Immunochemistry). (Fab)$_2$, Fab, Fv and ScFv fragments also can be obtained by recombinant technology by cloning genes coding-for variable regions of heavy and/or light antibody chains or portions of them bearing the sequences coding for antibody regions specifically recognizing a particular protein conformer or in a recombined form to obtain specific recombinant Fab or ScFv fragments.

For understanding and treating a disease in which peptide conformers are involved, it is useful to identify one or more antibodies that are substantially specific for the conformer. This method involves contacting a number of conformers with a number of antibodies, or binding fragments derived from specific antibodies. The specificity of binding of the antibodies or fragments to individual conformers is then evaluated. Antibodies or fragments that are substantially specific for each of the various conformers can thus be identified.

Pharmaceutical compositions of the invention are suitable for use in a variety of delivery systems for administration to humans, including administration parenterally, e.g., intravenously, subcutaneously, intradermally, intraperitoneally, or intramuscularly. The antigen formulations can also be delivered using implanted mini-pumps, which are well known to those skilled in the art. The compositions include formulations comprising one or more purified antigens as well as antibodies specific for a protein conformer of interest. The antibodies can be purified from sera from any animal in which antibodies to a protein conformer of interest can be raised. Preferably the antibodies are humanized. Humanized antibodies may-be produced in transgenic animals-that produce human antibodies. Humanized antibodies may also be produced by biochemical modification of nonhuman antibodies, for example, murine monoclonal antibodies, which may include fusing the antigen-binding or Fab portion of the murine monoclonal antibody with a non-binding or Fc region of a human antibody. Humanized antibodies generated by these and other methods retain desired antigen binding specificity, generally without causing an undesirable immune response to the antibody itself.

Examples of pharmaceutically acceptable carriers and formulations for use with the compositions of the present invention are found in Remington's *Pharmaceutical Sciences*, Mack Publishing Company, Philadelphia, Pa., 17th ed. (1985), which is incorporated herein by reference. For methods for drug delivery, see Langer, (1990) *Science* 249:1527-1533, which is incorporated herein by reference. For vaccine use and production, see Plotkin, et al. (eds.) (1999) *Vaccines*, 3rd edition. W.B. Saunders, Philadelphia, and Zegers, et al. (eds.) (1995) Immunological Recognition of Peptides in Medicine and Biology, CRC Press, Boca Raton, Fla., which reference is incorporated herein by reference. For mucosal vaccine delivery, see Ryan et. al., (2001) *Trends Biotechnol* 19: 293-304, and Ogra, et al., (2001) *Clin Microbiol Rev* 14:430-445, which are incorporated herein by reference. For examples of adjuvants, see Gregoriadis, G., ed., (1990) Immunological Adjuvants and Vaccines (NATO Asi Series A, Life Sciences, Vol 179), which is incorporated herein by reference.

In preparing pharmaceutical compositions of the present invention, it may be desirable to modify the compositions of the present invention to alter their, immunogenicity and biodistribution. For a general discussion of pharmacokinetics, see Remington's *Pharmaceutical Sciences*, supra, Chapters 37-39. A number of methods for altering pharmacokinetics, immunogenicity and biodistribution are known to one of ordinary skill in the art (See, e.g., Langer, supra, Gregoriadis, (1990), supra). Examples of such methods include protection of the agents in vesicles composed of substances such as proteins, lipids (for example, liposomes), carbohydrates, or synthetic polymers. For example, the vaccines of the present invention can be incorporated into liposomes in order to enhance their immunogenicity and biodistribution characteristics. Liposomes that microencapsulate vaccine antigens, and are then polymer-coated, are useful for controlling the release rate, and hence the efficacy, of parenterally and orally administered vaccines. A variety of methods are available for preparing liposomes, as described in, e.g., Szoka et al, (1980) *Ann. Rev. Biophys. Bioeng.* 9:467, U.S. Pat Nos. 4,235,871, 4,501,728 and 4,837,028, all of which are incorporated herein by reference. For a brief review of the use of liposomes as antigen-entrapping and delivering adjuvants or immunomodulators, see Gregoriadis (1999) *Methods* 19:156-162, and Rogers, et. al. (1998) *Crit Rev Ther Drug Carrier Syst* 15: 421-480, which are incorporated herein by reference. Polymeric lamellar substrate particles produced by precipitation of poly(D,L-lactide) form a polymeric system for the adsorption of antigens. This procedure avoids pH changes, exposure to organic solvents and hence allows the integrity of the antigen to be retained. For polymeric lamellar substrate particles for intranasal vaccination, see Jabbal-Gill et al. (2001) *Adv Drug Deliv Rev* 51: 97-111, which is incorporated herein by reference.

To prepare formulations for injection, a solution of the composition is dissolved or suspended in an acceptable carrier, preferably an aqueous carrier. A variety of pharmaceutically acceptable aqueous carriers can be used, e.g., water, buffered water, 0.4% saline, 0.85% saline solution, 0.3% glycine, hyaluronic acid and the like. The conjugate formulations may also comprise an adjuvant to stimulate an active immune response to the antigen. Examples of adjuvants are well known in the art and include, for example, aluminum hydroxide (Spectrum Chem. Mtg. Corp., New Brunswick, N.J.) or aluminum phosphate (Spectrum),calcium phosphate, saponins, monophosphoryl lipid A, Freunds adjuvant, liposomes, polymer-coated liposomes, polymeric lamnellar substrate particles, and cytokines such as interleukin-2.

The compositions can contain as pharmaceutically acceptable carriers, substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like, as well as preservatives including, for example, thimerisol, and protein carriers including, for example, human serum albumin or animal sera. The compositions can be sterilized by conventional, well-known sterilization techniques, including sterile filtration. The resulting aqueous solutions or suspensions can be packaged for use as is, or lyophilized, the lyophilized preparation being combined with a sterile solution prior to administration. For solid compositions, conventional non-toxic pharmaceutically acceptable carriers can be used which include, for example, pharmaceutical grades of mannitol, lactose, starch, magnesium stearate, sodium saccharin, talcum, cellulose, glucose, sucrose, magnesium carbonate, and the like.

Sequencing of the protein conformers to which monoclonal antibodies have been raised against shows that the conformer proteins contain essentially the same amino acid sequence as the native protein. Therefore, it is not necessary to develop an epitope map based on linear peptides but instead the protein preferably is mapped for conformational, or discontinuous, epitopes. The different specificity of the monoclonal antibodies is derived from the different folding of the same amino acid sequence. Thus, conformational epitope mapping is useful to show that the monoclonal antibodies are binding to restricted epitopes. Discontinuous epitopes can be identified using limited proteolysis of the antibody bound to a conformer of the protein of interest and then analyzing the lysate using mass spectrometry (MS) or three-dimensional imaging by NMR spectroscopy or crsyatllography. Monoclonal antibodies (MAb) are bound to a solid support and lysates containing the conformer protein are incubated with the immobilized Mab. Following removal of unbound protein, selected diluted proteases are added to the immobilized Mab-conformer complexes and unbound cleavage products are removed. The bound conformer proteins are eluted, under appropriate conditions, and analyzed by LC-MS. Sequencing of the conformer protein and molecular modeling generally are necessary to fully identify the conformational epitope.

Population profiles of conformers associated with disease severity or other characteristics can be developed by contacting a fluid of an individual with a conformer related disease, or infected cells from the individual, with one or more monoclonal antibody specific for a conformer involved in the disease. The fluid may be any bodily fluid including blood, serum, plasma, lymphatic fluid, urine, sputum, cerebrospinal fluid, or a purulent specimen. A binding fragment derived from a monoclonal antibody specific for a host protein and/or conformer also can be used. The monoclonal antibody or binding fragment is labeled with a detectable label, for example, a radiolabel or an enzyme label. Examples of enzyme labels that may be linked to an antibody include horseradish peroxidase, alkaline phosphatase, and urease, and methods for linking enzymes with antibodies are well known in the art. The label can be detected using methods well known to those skilled in the art, such as radiography, or serological methods including ELISA or blotting methods. The presence of the label is indicative of the presence of at least one protein or peptide conformer in the individual, and may be used to identify conformer profiles that play a role in the disease process. Detection of the label in a bodily fluid indicates the presence of at least one protein and/or peptide conformer thereof in the individual. A plurality of monoclonal antibodies or their binding fragments similarly can be used to detect a plurality of conformers associated with a disease state in an individual.

By detecting and characterizing conformers associated with a disease in a number of individuals in a population, a profile of the various conformers associated with the disease can be developed. Establishing a conformer profile in such a population is conducted by detecting and characterizing conformers associated with any given disease in individuals, compiling the data within the population, and then establishing the relationship between conformer profiles of the individual members of the population and specific characteristics of the disease in the individuals. These specific characteristics will depend on the disease and the nature of the protein or peptide conformer, and can be used not only for a definitive disease diagnosis but also for determining prognosis and developing an appropriate treatment for individual patients. For example, various peptide conformers may be associated with greater or lesser disease severity. As another example, peptide conformers may be associated with greater or lesser disease resistance. The response of individuals within the population to various disease treatments is an important factor in profiling the relationship between the conformer profile of an individual and his or her responsiveness. Individuals that respond poorly to treatment, for example, may have conformational forms of a protein or peptide involved in the disease process that make poorer targets for the treatment than the conformational forms of the protein or peptide in individuals that respond well to treatment. Population studies can be done to establish these relationships between conformers and response with a reasonable degree of significance.

Once a relationship between a conformer profile and treatment efficacy is established in a population, selection of a treatment for any given patient can be improved by determining the conformer profile an individual patient using, for example, the antibody- or antibody fragment-based methods described above. Those treatment regimens that have been established as successful for individuals with substantially similar conformer profiles to that of the instant patient are most likely to prove efficacious. Examples of populations profiles that can be developed include drug sensitivity, efficacy, and side effects, complications of disease or treatment. Also of interest is the ability to use said mAbs in conjunction with population-based patient profiles to localize any individual patient at a particular time within a subset of those population based profiles and to monitor the change in an individual patient's conformer mix and therefore in their membership in a predictive population-based cohort, as a function of change in age, drug therapy, diet and lifestyle.

The methods and compositions described herein have a number of uses. For example, the cell-free translation/assembly system can be used to produce large quantities of specific protein conformers. The protein conformers so produced can be used, for example for immunization or to produce vaccines. An antigen that selectively elicits a (humoral) immune response against one conformation and not another conformation of a given protein is applied in immunogenic amounts to a human or an animal. Conformation-selective humoral immune responses are elicited by immunization either with a "minimal peptide" that mimics the surface epitope of a conformational antibody or with a complete antigen that has been treated such by biochemical means and/or addition of additional molecular components that the humoral immune response is channeled to the one conformational epitope and not another ("monospecific conformational antibody response"). A minimal peptide is constructed after the exact knowledge about the three -dimensional surface-contacts between a specific antibody or derived ligand, and the antigen has been obtained. The amino acid residues that constitute the epitope are then engineered into one molecule by means of cyclization of linear peptide fragments and/or other chemical modifications.

Alternatively, the antigen-to-be-targeted is isolated from preparative samples of body tissue, bodily fluids or recombinant expression systems in the specific conformation. This preparation is then fixed by chemical modifications such as intra or intermolecular crosslinking; other biochemical means of "freezing" a conformation are immobilization with second, third or multiple molecules. These complexes are then further optimized such that a conformation-specific humoral immune response results by suppressing other epitopes that would not distinguish among different conformers of the protein in question. This can be achieved by digesting other immunogenic epitopes away with the help of specific proteases and/or protecting the other epitopes by chemical modifications. This "minimal epitope" molecule synthesized from peptides or the biochemically prepared "frozen" conformers are then applied to a test animal to confirm the conformational specificity and test for side-effects. Ultimately, the "minimal epitope" molecule is administered in a standard pharmaceutical immunization preparation and used to treat animals or humans with diseases where a specific conformer is at the cause of the pathological process. Generally, with conventional immunization techniques, it is expected that each dose will comprise about 1-1000 μg of total-immunogen, preferably about 2-100 μg, more preferably about 1-40 μg, and most preferably about 1-5 μg. Alternatively, if techniques according to Blachere et al., (1997) supra) and Castellino et al., (2000) supra) are used, the amount will be in the nano gram range. In this case, the purity of the conformer in the vaccine is of paramount importance. An optimal amount for a particular vaccine can be ascertained by standard studies involving observation of antibody titers and other responses in subjects. A primary vaccination course can include 2 or 3 doses of a vaccine, given one to two months apart, however, due to genetic and other factors, an antibody response to any vaccine preparation is likely to vary between preparations and individuals. Response to vaccination is monitored to determine both short and long-term vaccine efficacy, the former can be used for evaluating conjugate preparations and the latter for evaluating individuals as to their need for "booster" vaccinations. To determine antibody titer following vaccination, blood specimens from vaccinated animals are analyzed using standard techniques known to those skilled in the art such as by ELISA. Preferably, the blood specimens include samples from each patient before (i.e., a negative control) and about four weeks after vaccination and subsequently at intervals of about 2 to 6 months. As needed, a booster vaccination can be administered.

The conformers also find utility as reagents in screening assays for monoclonal antibodies that differentially bind to only one protein conformer and also can be used as a diagnostic for diseases that involve an infectious agent, such as prion-related diseases. The assay can be set up according to any of a number of formats. To screen for disease-related conformers monoclonal antibodies are used directly. High throughput screening of biological samples for disease associated conformers. For example, the biological sample is added to a solid phase immunocapture site coated with antibodies specific for one or more of the disease related conformers; binding is indicative of the presence of a disease related conformer in the biological sample. Such information can be used to identify potential treatments, or combination therapeutics against the infectious agent. Disease-related proteins to be evaluated for altered conformer ratios include insulin, insulin receptor and glucose transporters (diabetes mellitus), prostatic acid phosphatase (prostate cancer), leptin (disordered satiety and obesity), nogo-alb (neuronal regeneration inhibitor), viral capsid molecular chaperones such as hp68 (HIV), and prion protein.

The monoclonal antibodies specific for a particular disease-associated conformer can be used for either diagnostic purposes, when correlated with a population of patients with a particular natural history, disease outcome or other clinical epidemiological finding, or for passive immunization when the intent is to modify the conformer-specificity of a biological response. To achieve the latter, a monoclonal antibody specific for a particular disease-associated conformation, or a recombinant form of the same is purified to remove any pyrogenic contaminants or toxic by -products of production and prepared in a pharmaceutical composition and administered to a human or other animal in need of treatment for a disease associated with the conformer. Generally the composition is administered intravenously. Alternative application routes include local application, for example on wounds or mucous tissue, depending on the particular pathophysiology of the disease process and the accessibility of the disease-causing conformer. Passive immunization is an established pharmacological therapy; see for example manufacturer information relating to administration of trastuzumab (HERCEPTIN®, Roche), daclizumab, abciximab, and the like.

Conveniently, the formulations can be provided in single dose kits in sterile vials so that the physician may employ the vials directly, where the vials will have the desired amount and concentration of formulation. When the vials contain the formulation for direct use, usually there will be no need for other reagents for use with the method. The subject compositions can be contained in packaging material, which comprises a label indicating that the subject compositions can be used to treat a protein conformer related disease in humans.

The following examples are offered by way of illustration of the present invention, not limitation.

EXAMPLES

Materials and Methods:
Buffers Used:
Homogenisation Buffer:
0.25 M Sucrose (Sigma, USA)
50 mM Hepes (Sigma, USA)
100 mM Potassium acetate (Merck, Germany)
5 mM Magnesium chloride (Sigma, USA)
Sample Loading Buffer:
50 mM Tris-Cl (pH 6.8) (Merck, Germany)
2% SDS (w/v)(Sigma, USA)
2% β-mercaptoethanol (Sigma,USA)
10% glycerol (Sigma, USA)
2% □-mercaptoethanol (Sigma, USA)
12% SDS Gels were poured as described by Sambrook & Russell (2001) Molecular Cloning. A laboratory manual. Cold Spring Harbor Laboratory Press, New York, USA;
Reagents from BioRad (USA): Acrylamide, TEMED or Sigma (USA):
Ammoniumpersulfate, SDS; apparatus from Biometra Inc., Germany.
Gel Running Buffer:
25 mM Tris base (Merck, Germany)
250 mM Glycine pH 8.3 (Sigma, USA)
0.1 % SDS (w/v) (Sigma, USA)
Gel Transfer Buffer:
12 h transfer on polyvinylidene fluoride (PVDF) membranes (Millipore, USA) at 200 mA.
48 mM Tris base (Merck, Germany)
39 mM glycine (Sigma, USA)
20% methanol (Merck, Germany)
Optional Ponceau Staining:
1 g Ponceau S (Sigma, USA) in 5% Acetic acid (Merck, Germany)
Tris-buffered Saline with Tween 20 (TBS-T):
8 g Sodium chloride (Merck, Germany)
0.2 g Potassium chloride (Merck, Germany)
3 g Tris base (Merck, Germany)
in 1000 ml H$_2$O, add 500 µl Tween 20 (0.05%) (Boehringer Ingelheim, Germany)
pH adjusted to 7.8
Blocking Buffer:
5% low-fat milk (Oxoid, United Kingdom)
in TBS-T
Copper Stocks:
500 mM or 25 mM copper (II) sulfate pentahydrate (Merck, Germany)
in ultrapure water, sterile filtered

Example 1

Preparation and Analysis of Binding Characteristics of Conformer Specific Monoclonal Antibody to Prion Protein

Antibody Production:
7VC hybridoma cells (which cells were deposited at American Type Culture Collection (ATCC) 10801 University Blvd. Manassas, Va. 20110-2209 on Feb. 2, 2010, under the Budapest Treaty, accession number SOC25016) were grown in protein-free hybridoma medium (PFHM II; #12040-051 Gibco/Invitrogen, USA) containing OptiMAb (#11910-031 Gibco/Invitrogen, USA) in a 75 ml tissue culture flask. They were harvested shortly after the incubation medium began to discolor to a more yellowish color tone, in order to have maximal antibody concentration but minimal cell death. The antibody concentration was then measured by comparing the supernatant mAB concentration to a known one by Western blotting. It was around 100 µg/ml.

Experimental Protocol:
All Western blots were performed using the following protocol:
1. 0.5% brain homogenates of hamsters or transgenic mice, as specified, were loaded in same amounts on a 12% SDS gel (run at 35 mA current) and transferred to a PVDF membrane by immersion (wet) blotting for 12 hours at constant current 200 mA.
2. Membranes were then optionally stained with Ponceau S in TBS-T to visualize individual lanes and control transfer of proteins.
3. After washing in TBS-T, membranes were blocked with 5% low-fat milk in TBS-T for 1 hour.
4. "Normal Washing" includes three alternating washing cycles in Millipore -generated water (1 minute) and TBS-T (5 minutes); "Intensive washing" includes four alternating washing cycles in Millipore-generated water (1 minute with 3 fold rinsing), and increasing TBS-T washing steps for initial five, and then ten minute cycles.
5. After blocking, membranes were intensively washed and, eventually, cut into individual strips. Small strips were incubated in 15 ml Falcon tubes (Greiner, Germany).
6. Antibody was added to a final concentration of 10 µg/ml into TBS-T and a defined concentration of copper sulfate or 100 mM EDTA, added from a stock solution. Primary antibody was incubated for 2 hours at room temperature on an orbital shaker.
7. Blots were intensively washed.
8. Secondary antibody (Goat anti-mouse IgG H/L-peroxidase labeled; #31444 Pierce, USA) was incubated in a 1:5000 dilution for 1 hour.
9. Blots were intensively washed. A final wash was with water before enhanced chemiluminescent (ECL; Amersham Pharmacia, USA) substrate was added, and developed with Hyperfilm (Amersham Pharmacia, USA).

Range of Differential Binding:
At pH 7.8 of the TBS-T incubation buffer, a differential binding profile was established for detection of PrPCTM (PrP immunoreactivity in Tg(KH>II) mouse brains vs. PrP secretory (PrP immunoreactivity in Tg(7BHOZ) mouse brains). It was found that differential immunoreactivity of Tg(KH>II) was present in CUSO$_4$ concentrations between 1 µM and 50 µM. Higher concentrations significantly weakened immunoreactivity, and eventually completely stripped off the antibody from the blot. Lower concentrations gave inconsistant results with no clear distinction; therefore 100 mM EDTA was added to chelate out metal ions randomly present in blots and buffers.

At fixed antibody (10 µg/ml) and copper (25 µM) concentrations, pH in TBS-T was varied, it was found, that at pH 5 all immunoreactivity was abolished, at pH 7.8 immunoreactivity was differential between Tg(KH>II) and Tg(7BHOZ) brains, and positive but not differential at pH 9.

Example 2

Identification of a Monoclonal Antibody that Binds to NTM PrP

Figure 8:
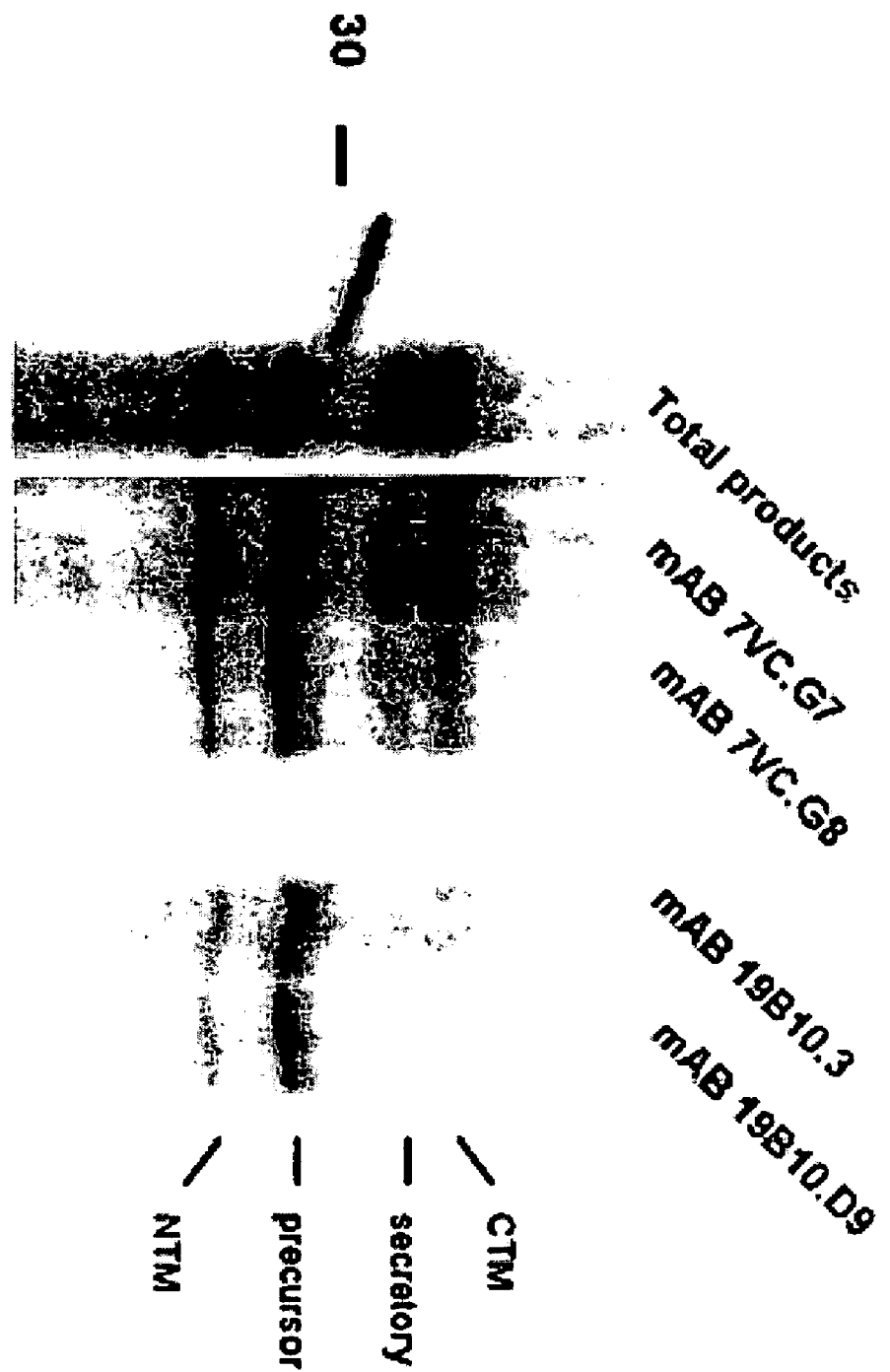
FIG. 8 shows in vitro translation of PrP (leftmost lane), and immunoprecipitations with clones of 7VC (lane 2 and 3), and 19B10 (lanes 4 and 5).
Figure 9:
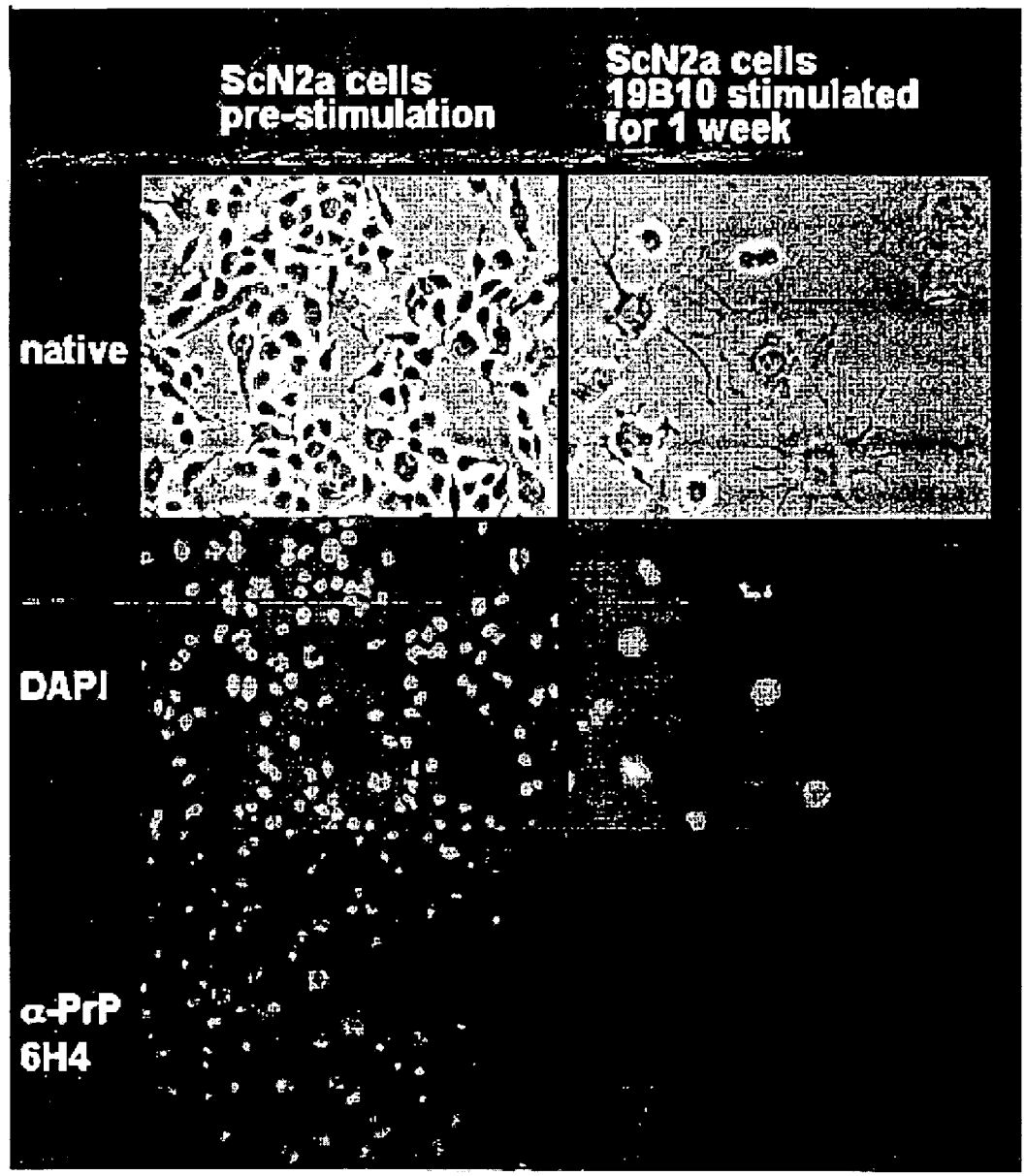
FIG. 9 shows ScN2a cell differentiation after treatment with 19B10 for 1 week.

In vitro translated PrP isoforms were prepared as described in U.S. Ser. No. 09/739,179, filed Dec. 15, 2000 and published Sep. 26, 2002 as US-2002-0137915-A1, which disclosure is incorporated herein by reference. The conformational isoforms produced were screened by immunoprecipitation with monoclonal antibodies prepared using methods known to those of skill in the art and previously shown to interact with PrP (see for example the results in Example 1, above). In vitro translation of PrP isoforms is shown in FIG. 8 (leftmost lane), and immunoprecipitation with clones of 7VC (lane 2 and 3), and 19B10 (lanes 4 and 5). 19B10 does not recognize secretory or CTM PrP but only NTM PrP and precursor PrP.

Example 3

Localization of PrP Isoforms in Scrapie-infected Neuroblastoma Cells

Permanently scrapie-infected neuroblastoma cells (ScN2a) were used that had been derived from infection of neuroblastoma cells (N2a cells; ATCC # CRL 131) with the RML strain of mouse-adapted scrapie (Chandler et al. 1961 *The Lancet* i: 1378-1379) and subsequent subcloning (Bosque and Prusiner, J. Virology 74: 4377-4386).

Immmunostaining of the cells was performed as described in Korth et al., (2000) *Journal of General Virology* 81: 2555. Antibody suspensions used for 7VC and 19B10 were cell culture supernatants from HT medium (Minimal Essential medium (INVITROGEN™/Gibco # 21090-022), supplemented with 10% FCS (PAA Laboratories, Linz, Austria) and 100 U/ 100 ug/ml penicillin/streptomycin, respectively, final concentration, with hypoxanthine and thymidine (both from Sigma, USA) added to 1.36 and 0.76 mg/100 ml final concentration, respectively) in a concentration 1:1 with Phosphate-buffered saline.

Immunostaining of ScN2a cells was performed without antibody with mAB 6H4, with mAB 19B10 and with mAB 7VC. Immmunostaining was performed on the cell surface, or after permeabilization with saponin (Sigma, USA) for intracellular staining.

The results indicated, mAB 7VC stains both the cell surface and the intracellular compartments of ScN2a cells. MAB 19B10 stains the cell surface of ScN2a cells indicating that-NTMPrP is present on the cell surface of these cells. MAB 19B10 does not stain the intracellular compartments when cells are permeabilized with saponin; this is likely due to denaturation of the NTMPrP conformation by the saponin.

Example 4

Differentiation of Scrapie-infected Neuroblastoma Cells with 19B10

ScN2a cells are N2a cells are taken from a confluent 10 cm cell culture dish and split into a 60 mm dish (1 drop). They are grown in Minimum Essential Medium supplemented with 10% FCS and penicillin/streptomycin as described above. Different concentrations of hybridoma cell culture medium supernatant (HT medium, see above) were added (0.5%, 1%, 5%, 10%, 50%, and HT medium alone as a control). Medium and added HT medium supernatants were changed every other day for a week. After 7 days of treatment, and not before, and only in a tight concentration range of 5-10% HT medium added (corresponding to final mAB concentration of 24 µg/ml cell culture medium) it was observed that massive cell death was occuring but the remaining ScN2a cells were differentiating to giant cells (compare FIG. 10 upper panel left to right picture). This was accompanied by apoptotic-like bleeding of some nuclei (FIG. 10 middle panel) and down-regulation of total PrP expression (FIG. 10, lower panel), as seen by intracellular PrP staining with mAB 6H4, performed as described in Korth et al., (2000) *Journal of General Virology* 81: 2555.

Treatment of ScN2a cells (and also N2a cells, data not shown) with mAB 19B 10 leads to a dose-dependent effect that includes cell death and differentiation of remaining cells. For reasons still unknown, mAB 19B10 concentrations≧50% (≧10 µg/ml) do not have this effect. It is also unknown why the effect is rather sudden—but reliable—after about 1 week of treatment. Targeting PrP with other antibodies (e.g. 7VC or 6H4) does not lead to these effects. Quite uniquely, targeting NTM PrP by mAB 19B 10 leads to a general downregulation of PrP (as seen by immunostaining).

Example 5

Inhibition of Prion Replication by Conformer-specific Monoclonal Antibodies

ScN2a cells were treated as described in Example 4, above. After one week, the cells were lysed and processed exactly as described in Korth et al. (2001) PNAS 98:9836. Results indicated that mAB 7VC inhibits prion replication in ScN2a cells. MAB 19B10 inhibits prion replication in ScN2a cells only at concentrations of 10% (ca. 4 ug/ml) but not at concentrations≧50% (10 ug/ml) or lower 5% (2 ug/ml). The antiprion effect of mAB 19B10 contrasts with those of other mABs, including 7VC. "Conventional" mABs shield PrPC (likely the secretory form) from being converted (Peretz et al., (2001) *Nature* 412: (6848):739-43), whereas 19B10 acts by downregulating PrP expression.

Example 6

Varying Copper Dependency of Different PrP Species

Figure 10A:
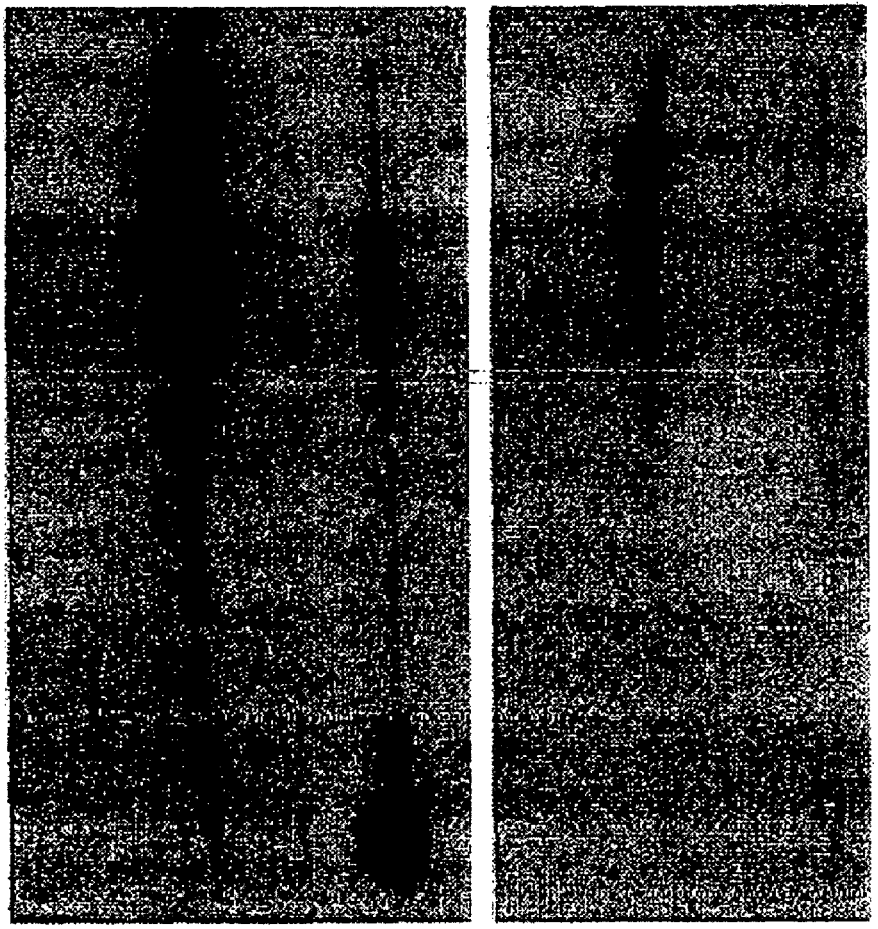
FIG. 10a shows a Western blot demonstrating the effects of eluates with different copper concentrations after immunoprecipitation of 7BHOZ brain homogneate (transgenic mouse expressing Syrian hamster PrP; upper panel) or F1198 brain homogenate (transgenic mouse expressing mutated Syrian hamster PrP with increased CTMPrP; lower panel).

Brains were homogenized in 0.25 M sucrose, 150 mM potassium acetate, and 5 mM magnesium chloride ("buffer A") to a 10% homogenate with a Dounce homogenizer. Homogenates were then diluted to 1% and precleared by centrifugation in a table top centrifuge at 1000 rpm for one minute. Then, 1.5 ml of the precleared 1% homogenate and ca. 5 ug mAB 7VC grown in serum-free medium, and protein A-agarose were incubated overnight at 4° C. The agarose containing proteinA-bound 7VC and immunoprecipitated PrP was then spun down by a short (ca. 10 seconds) 1000 rpm spin in a table top centtrifuge and washed with buffer A three times. Subsequent elutions with 50 ul of sterile water containing increasing concentrations of copper sulfate ($CU_2SO_4$) were taken and run on a SDS gel. A Western blot showing eluates with different copper concentrations after immuno-precipitation of 7BHOZ brain homogneate (transgenic mouse expressing Syrian hamster PrP; FIG. 10*a*, upper panel) or F1 198 brain homogenate (transgenic mouse expressing mutated Syrian hamster PrP with increased CTMPrP; FIG. 10*a*, lower panel) As shown, mAB 7VC binds in a copper-dependent manner to different PrP species in solution. In the homogenate where CTMPrP is present, even high concentrations of copper cannot completely elute PrP ("gel"-lane); in addition there are PrP species that elute with high concentrations of copper in the CTMPrP containing homogenate but not the normal homogenate.

Figure 10B:
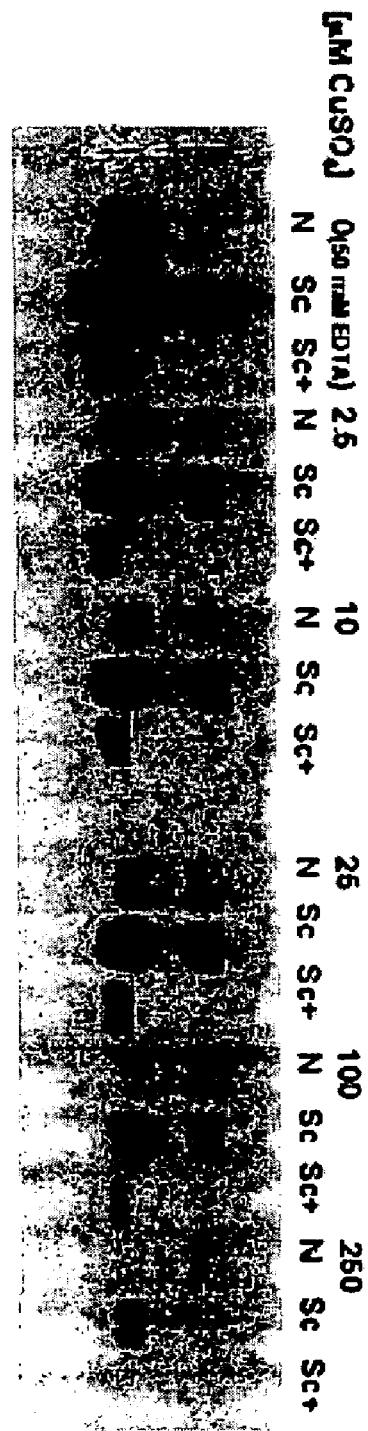
FIG. 10b shows Western blots of pro tease-undigested normal Syrain Hamster brain homogenate, scrapie-infected (Sc237 strain) Syrian Hamster brain homogenate, and protease digested scrapie-infected Syrian Hamster brain homogenate.

Western blots of protease-undigested normal Syrian Hamster brain homogenate, scrapie-infected (Sc237 strain) Syrian Hamster brain homogenate, and protease digested scrapie-infected Syrian Hamster brain homogenate prepared as described in Example 1, above are shown in FIG. 10b. PrP from different brain homogenates blotted on a membrane has different copper-dependent affinities for mAB 7VC. In particular, the immunoreactivity of PrP from normal brain is more easily abolished by copper, as compared to that from scrapie-infected brain. Since both homogenates have been boiled in SDS prior to gel electrophoresis, there are features in PrP that can "survive" this denaturation procedure and lead to some refolding on the membrane that then makes the described differences apparent. Using the present procedure, mAB 7VC can distinguish scrapie-infected brain form non-infected brain in a copper-dependent manner Example 7

Binding of Conformer Specific Antibodies to Different Brain Homogenates

Figure 11:
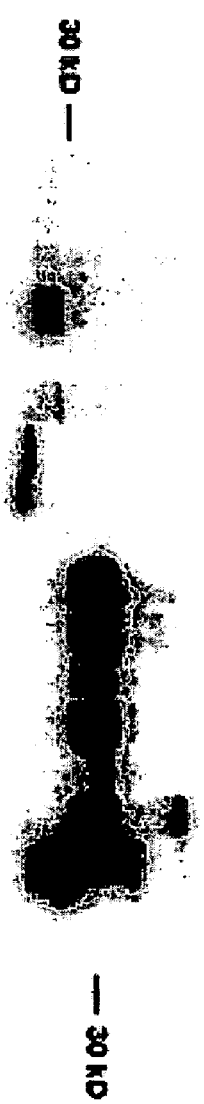
FIG. 11 shows a Western blot of different brain homogenates with mABs 7VC, 19B10 and 6H4.
Figure 11:
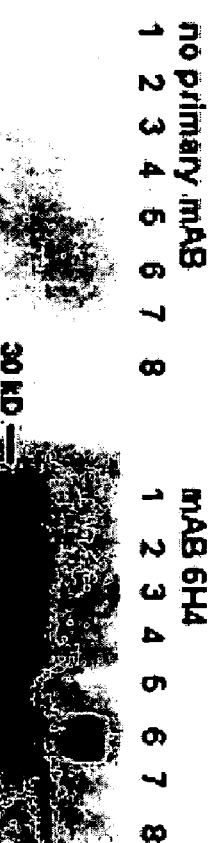

A Western blot of 10% brain homogenates in buffer A prepared as described above were used and incubated with mABs 7VC, 19B10 and 6H4. The results are shown in FIG. 11. mAB 7VC binds to the octarepeats, therefore it cannot immmunologically recognize moPrP with the octarepeats deleted (FIG. 11, lower panel to the right, compare lane 7 and 8). mAB 19B10 has generally weak immunoreactivity. The strongest immunoreactivity is in brain homogenates of transgenic mice in which PrP expression suppressed by expression under the tetracycline promoter; if the tetracycline promoter is removed, PrP expression is induced, and mice become ill with signs of neurological illness. These mice likely produce aberrrant isoforms of PrP, likely including CTMPrP and NTMPrP.

Example 8

Preparation of Conformer Specific Monoclonal Antibodies and their Use in Patient Profiling A denatured or native antigen is used to immunize a mouse, and hybridomas generated by fusion of spenocytes with myeloma cells. The resulting hybridomas are screened by solution IP against conformer-enriched cell-free translation products or conformer-containing tissue slices or cells by immunostaining, or by western blot, identifying the few, often weak reactors, that are purely conformation specific. A patient's serum or isolated and lysed "buffy coat" from a centrifuged anticoagulated blood sample, is then used as an "unknown" by reference to the known cell-free translation conformers, and is screened by solution IP, western blot or immunostaining for relative reactivity to antibodies specific to different conformers to generate a conformer index profile that reflects the relative ratios of one conformer to the others in that particular patients serum at the time the blood was drawn. Changes in profile can be determined by population and retrospective clinical epidemiological correlation and can be monitored as a function of time, drug therapy, diet and lifestyle or other change to correlate the prospective condition of any given patient with the population based cohort.

Example 9

Immunization Against Prion Disease $PrP^{CTM}$ is synthesized with an in vitro translation system as described by Hay et al., 1987 Mol. Cell Biol. 7:914-919; Hegde et al. (1998) supra and Hegde et al (1999) supra. Mutated PrP constructs are used such that individual PrP conformers are favored. For the immunization procedure, methods developed by Srivastava and colleagues are used (see (Blachere et al., (1997) supra and (Castellino et al., (2000) supra). Briefly, recombinant (mouse or other species) HSP70 (1-10 µg) and the antigen, in vitro translated $PrP^{CTM}$ (as much as possible, but at least 50 ng) are incubated together with PBS containing 1 mM KCl, 2 mM $MgCl_2$ and 100 µM ATP for 60 min at RT in an appropriate volume; finally, 1 mM ADP is added and incubated for 30 min. This is the antigen. The antigen is then used for immunization of the desired animal by either intracutaneous subcutaneous, intramuscular, intraperitoneal or intravenous route according to standard protocols. Optionally, adjuvants such as Freund's complete adjuvant, RIBI or aluminum hydroxide (all from Sigma, U.SA), or a recombinant cytokine such as interleukin-2 is used.

Example 10

Passive Immunization with Conformation-specific Antibodies

Passive immunization involves prior identification of a disease-associated conformer of a protein. Monoclonal antibodies or derivatives thereof having the desired differential binding specificity are produced as described above. These monoclonal antibodies are processed so that they are physiologically acceptable and meet appropriate pharmacological standards for their administration. Usually, antibodies are highly purified, pyrogens are extracted, and possible immunogenic epitopes on the monoclonal antibody suppressed by genetically modifying the monoclonal antibody (e.g. "humanized antibodies"). A pharmaceutical preparation of the antibody is then provided to an animal in need thereof according to the disease phenotype, and the location of the disease, intravenously, subcutaneously, intramuscular, intraventricularly, intraperitoneally, or locally on cutaneous or mucous tissue. This treatment is repeated for as long as symptoms of the disease persist and protection is established.

Example 11

Production of Conformation Sensitive Antibody Chips

Conformation-sensitive antibody chips for profiling of patient tissue or fluid samples for high-throughput diagnosis are prepared as follow. A panel of conformation-specific antibodies raised according to methods detailed above is covalently fixed on a particular microarray, preferably an addressable microarray. There is no limit in the number of conformation-specific antibodies to be used since the individual differences of reactivities of individual antibodies (in fixed amounts) with respective tissue or fluid samples is monitored and documented. The greater the number of antibodies that are used, the higher the profiling potential. Since the microarrays are manufactured by standard procedures (see for example manufacturer's instructions from Affymetrix or Ciphergen,) and operate on a micro- to nanoscale, hundreds of monoclonal antibodies are used. A tissue sample or bodily fluid in an appropriate buffer solution is contacted with the chip and any unbound materials removed by washing. Binding is detected for example by biophysical means (e.g. laser scanning and/or plamon resonance measurement, fluorescence quenching) or immunologically. Examples of detection procedures include those used with antibody chips (Becton & Dickinson, Ciphergen, and others). The presence of particular conformers is evidenced by detection of binding to the monoclonal antibodies immobilized on the chip. Presence or absence of particular conformers is then used to develop a profile for the patient.

As is shown above a unique molecular structure in PrPCTM (that is also associated with PrP$^{Sc}$) has been identified using a monoclonal antibody that can differentially recognize this molecular structure. This unique molecular component associated with PrPCTM and PrP$^{Sc}$ can be stained with mAB7VC under conditions of defined excess copper ions present near the binding site of mAB 7VC. At pH 7.8 of the TBS-T incubation buffer, a differential binding profile was established for detection of PrPCTM (PrP immunoreactivity in Tg(KH>II) mouse brains vs. PrP secretory (PrP immunoreactivity in Tg(7BHOZ) mouse brains). It was found that differential immunoreactivity of Tg(KH>II) was present in CuSO$_4$ concentrations between 1 µM and 50 µM. Higher concentrations significantly weakened inmmunoreactivity, and eventually completely stripped off the antibody from the blot Lower concentrations gave inconsistant results with no clear distinction; therefore 100 mM EDTA was added to chelate out metal ions randomly present in blots and buffers. At fixed antibody (10 µg/ml) and copper (25 µM) concentrations, pH in TBS-T was varied. It was found, that at pH 5 all immunoreactivity was abolished, at pH 7.8 immunoreactivity was differential between Tg(KH>II) and Tg(7BHOZ) brains, and positive but not differential at pH 9. This molecular component is either a covalent modification or an extremely tight folding of the protein, or both Molecular targeting of mAB 7VC towards this structure now enables differential recognition of PrPCTM or PrP$^{Sc}$ from other PrP species.

A second mAB has been identified, 19B10 that differentially binds to PrPNTM and stains the cell surface of ScN2a cells. Addition of the antibody to cultured N2a or Sc2a cells leads to a reduction in cell number and differentiation of the surviving cells after one week of treatment at intermediate concentrations of about 25 to 250 µg/ml. Treated cells become larger, have more axonal extensions, and PrP expression (all conformational isoforms) is downregulated. The treatment is reversible. N2a cells are more sensitive to the treatment and reversal of the effects is faster than with ScN2a cells. It is an hypothesis of the invention that the 19B10 mAB binds to unglycosylated and monoglysocylated forms of PrP.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

The invention now having been fully described, it will be apparent to one of ordinary skill in the art that many changes and modifications can be made thereto without departing from the spirit or scope of the appended claims.

What is claimed is:

1. A method of detecting prion disease in a sample, said method comprising: contacting said sample with a diagnostically effective amount of the monoclonal antibody designated 7VC; and determining whether said antibody binds specifically to any material in said sample under conditions whereby differential binding of said antibody to PrP isoforms associated with prion disease occurs, wherein antibody binding is indicative of prion disease.

2. The method according to claim 1, wherein said sample is a tissue or a bodily fluid.

3. The method according to claim 1, wherein said conditions comprise a concentration of $Cu^{2+}$ ions in an amount that promotes said differential binding.

4. The method according to claim 3, wherein said concentration is about 1 μM to about 50 μM.

5. The method according to claim 1, wherein said conditions comprise a pH of about 7.8.

* * * * *

SEQUENCE LISTING

```
<160> NUMBER OF SEQ ID NOS: 4

<210> SEQ ID NO 1
<211> LENGTH: 15
<212> TYPE: PRT
<213> ORGANISM: Prion

<400> SEQUENCE: 1

Pro Gln Gly Gly Gly Thr Trp Gly Gln Pro His Gly Gly Gly Trp
1               5                   10                  15

<210> SEQ ID NO 2
<211> LENGTH: 15
<212> TYPE: PRT
<213> ORGANISM: Prion

<400> SEQUENCE: 2

Trp Gly Gln Pro His Gly Gly Gly Trp Gly Gln Pro His Gly Gly
1               5                   10                  15

<210> SEQ ID NO 3
<211> LENGTH: 14
<212> TYPE: PRT
<213> ORGANISM: Prion

<400> SEQUENCE: 3

Gly Trp Gly Gln Pro His Gly Gly Gly Trp Gly Gln Pro His
1               5                   10

<210> SEQ ID NO 4
<211> LENGTH: 15
<212> TYPE: PRT
<213> ORGANISM: Prion

<400> SEQUENCE: 4
```

-continued

```
Gly Gly Gly Trp Gly Gln Gly Gly Thr His Asn Gln Trp Asn
1           5               10              15
```